United States Patent
Lucas

(10) Patent No.: US 9,539,282 B2
(45) Date of Patent: Jan. 10, 2017

(54) THERAPEUTIC USE OF HYDROGEN MOLECULES

(71) Applicant: MAX-PLANCK-GESELLSCHAFT ZUR FORDERUNG DER WISSENSCHAFTEN E.V., Munich (DE)

(72) Inventor: Kurt Lucas, Hamburg (DE)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 14/431,176

(22) PCT Filed: Sep. 25, 2013

(86) PCT No.: PCT/EP2013/069911
§ 371 (c)(1),
(2) Date: Mar. 25, 2015

(87) PCT Pub. No.: WO2014/048953
PCT Pub. Date: Apr. 3, 2014

(65) Prior Publication Data
US 2015/0258136 A1    Sep. 17, 2015

(30) Foreign Application Priority Data
Sep. 26, 2012   (DE) ........................ 10 2012 217 387

(51) Int. Cl.
*A61K 33/00* (2006.01)
*A61K 31/198* (2006.01)
*A61K 31/375* (2006.01)
*A61K 31/60* (2006.01)

(52) U.S. Cl.
CPC ............. *A61K 33/00* (2013.01); *A61K 31/198* (2013.01); *A61K 31/375* (2013.01); *A61K 31/60* (2013.01)

(58) Field of Classification Search
None
See application file for complete search history.

(56) References Cited

U.S. PATENT DOCUMENTS

| 5,948,443 A | * | 9/1999 | Riley | ................... A23L 33/16 424/638 |
| 2002/0122834 A1 | | 9/2002 | Trant | |
| 2007/0148256 A1 | | 6/2007 | Yanagihara | |

FOREIGN PATENT DOCUMENTS

EP    2057990    5/2009

OTHER PUBLICATIONS

Nakao et al. "Effectiveness of Hydrogen Rich Water on Antioxidant Status of Subjects with Potential Metabolic Syndrome—An Open Label Pilot Study", J. Clin. Biochem. Nutri., 46, 140-149, Mar. 2010.*
Ferretti et al., Peroxidation of lipoproteins in multiple sclerosis, J Neurol Sci. 2011; 311(1-2): 92-7.
Hong et al., Hydrogen as a Selective Antioxidant: A Review of Clinical and Experimental Studies, J Intl Medical Research 2010; 38:1893-1903.
Imai et al., Identification of oxidative stress and Toll-like receptor 4 signaling as a key pathway of acute lung injury, Cell 2008; 133(2): 235-49.
Nakao et al., Effectiveness of Hydrogen Rich Water on Antioxidant Status of Subjects with Potential Metabolic Syndrome—An Open Label Pilot Study, J Clin Biochem Nutr 2010; 46:140-149.
Ueda et al., Hydrogen-Related Enhancement of In Vivo Antioxidant Ability in the Brain of Rats Fed Coral Calcium Hydride, Neurochem Res 2010; 35:1510-1515.

* cited by examiner

*Primary Examiner* — Susan Tran
(74) *Attorney, Agent, or Firm* — Casimir Jones, S.C.; Mary Ann Brow

(57) ABSTRACT

The invention concerns a kit for preventing or treating oxidative stress in humans or animals by means of therapeutically active hydrogen molecules. The hydrogen molecules are formed by reacting a base metal with aqueous acids or bases and by reacting a saline hydride with water or aqueous acids.

13 Claims, No Drawings

THERAPEUTIC USE OF HYDROGEN MOLECULES

This application is a §371 U.S. National Entry of International Application No. PCT/EP2013/069911, filed Sep. 25, 2013, which claims the benefit of German Patent Application 102012217387.0, filed Sep. 26, 2012.

The invention relates to a kit for prophylaxis or treatment of oxidative stress in humans or animals. The invention further relates to compositions and methods for providing therapeutically active hydrogen to eliminate free radicals from tissues in humans or animals.

It is known that oxidative stress, i.e. a quantity of reactive oxygen species (ROS) exceeding physiological levels, causes physical damage that becomes manifest in various clinical conditions and is described in more detail below. There is a large number of diseases of the human body in which free chemical radicals, but particularly reactive oxygen species, are generally involved. Radicals are taken in from the environment (air, food, water) or formed by the body itself. It is the biological function of ROS in the body to kill microbes (bacteria, fungi, viruses). But these radicals are themselves harmful to the body and can modify endogenous substances, such as lipids, hyaluron, and proteins. In this process, some substances are formed, e.g. oxidized phospholipids, which cause other inflammatory reactions by activating, for example, toll-like receptors (TLR2 and TLR4) and thus ultimately cause an additional release of ROS.

It is known from prior art that hydrogen, if inhaled or dissolved in water, is capable of rendering free radicals harmless in the body. One product is commercially available under the name: "One Stick of Doctor Suisosui", which is used to enrich water with hydrogen. The hydrogen-enriched water is drunk and the hydrogen is absorbed by the body.

It is a disadvantage of the "One Stick of Doctor Suisosui" product that the release depends significantly on the pH of the water used. The pH of drinking water can range from acidic to alkaline. Considerably less hydrogen, if any, is released in alkaline water. Thus the chemical conditions are not controlled, leading to a result that is not reproducible. According to a product video, the incubation time of "One Stick of Doctor Suisosui" in drinking water is two hours. The long preparation time required to obtain water enriched with hydrogen is a disadvantage. It is another disadvantage that the quantity of hydrogen that is released can vary considerably due to the variable incubation time. The "One Stick of Doctor Suisosui" product is designed to be reusable. The release of hydrogen becomes more and more uncertain due to increasing aging and wear. The product does not meet the requirement of providing a pharmacologically defined dose of hydrogen. In addition, the purchase price is rather high, so considerable costs are incurred. The product is primarily meant for home use; it appears to be less suitable to be comfortably taken along on trips. Targeted provision of hydrogen in specific tissues or organs (stomach, bowel) is not possible with this product.

The problem addressed by this invention is that of very substantially avoiding the disadvantages mentioned above, and in particular to provide therapeutically active hydrogen to be taken in order to render radicals harmless in biological tissues. One problem is to provide a reproducible supply of therapeutically active hydrogen. External circumstances, such as the pH of the drinking water used, should not have any major influence on the production of the hydrogen. Another problem is to make the hydrogen available in a timely manner, within a few minutes, in reproducible quantities. Producing hydrogen is to be possible at any time, including outside the home, such that a compact and transportable form is provided. Furthermore, other ways of delivering hydrogen should be made available for specific purposes when the goal is to supply specific organs and tissues with hydrogen in a targeted manner. Furthermore, an advantage is gained by combining the therapeutically active hydrogen with other substances (such as acetylsalicylic acid and/or ascorbic acid), which make it possible to achieve pharmaceutical synergistic effects.

The invention solves the problem with a kit according to claims 1 and 6. Advantageous embodiments of the invention are disclosed in the dependent claims.

The kit according to the invention is used for prophylaxis or treatment of oxidative stress in humans and animals using therapeutically active hydrogen molecules, wherein the kit comprises a first component including a base metal or a saline hydride for targeted chemical synthesis of the hydrogen molecules by reaction with endogenous or exogenous water and/or aqueous acid. The kit may also advantageously comprise a second component, wherein the second component includes water and/or at least one acid which is chemically inert with respect to the base metal or saline hydride of the first component. For example, one or more of the components that react with one another with release of hydrogen may be encapsulated to prevent a premature reaction of these components. According to a preferred embodiment of the invention, the therapeutically active hydrogen molecules are formed by combining the base metal or saline hydride of the first component with the acid under aqueous conditions and/or with the water of the second component. In another preferred embodiment of the invention, the human or animal is thus preferably supplied at least 0.4 mmol or 0.8 mg of molecular hydrogen per day.

Base metals within the meaning of this invention are metals that are decomposed by acids with evolution of hydrogen. These metals are preferably selected from the group consisting of magnesium, sodium, potassium, calcium, manganese, zinc and iron, beryllium, titanium, manganese, tin, boron, and aluminum, particularly preferably selected from the group consisting of magnesium, zinc, and iron.

Acids within the meaning of this invention are any acids that evolve hydrogen in aqueous solution with metals. The acids are preferably selected from the group consisting of ascorbic acid, acetylsalicylic acid, aminosalicylic acid, citric acid, and tartaric acid.

Saline hydrides within the meaning of this invention are ionic compounds that contain the hydride ion $H^-$ in combination with strongly electropositive metals of the first and second main groups of the periodic table of the elements (base metals) except beryllium. The saline hydrides form hydrogen when combined with water or acids. The saline hydrides are preferably selected from the group consisting of magnesium hydride, calcium hydride, sodium hydride, and potassium hydride, particularly preferably selected from the group consisting of magnesium hydride and calcium hydride.

According to a particularly preferred embodiment of the invention, the kit according to the invention includes magnesium as base metal, preferably in a quantity of 0.1 mg to 20 mg, and as acid includes an acid selected from the group consisting of ascorbic acid, acetylsalicylic acid, 5-aminosalicylic acid, citric acid, and tartaric acid, preferably in a quantity of 1 mg to 1 g.

In an alternative embodiment of the invention, the kit for prophylaxis or treatment of oxidative stress in humans or animals using therapeutically active hydrogen molecules comprises a first component including a base metal for targeted chemical synthesis of the hydrogen molecules by reaction with an aqueous base. The base can be added to the kit as another, that is, a second component, wherein in this case the base is chemically inert with respect to the base metal of the first component. For example, one or more of the components that react with one another with release of hydrogen may be encapsulated to prevent a premature reaction of these components with one another. According to a preferred embodiment of the alternative embodiment described, the therapeutically active hydrogen molecules are formed by combining the base metal of the first component with the aqueous base of the second component, and further preferably at least 0.4 mmol or 0.8 mg of molecular hydrogen per day is supplied to a human or animal.

Bases within the meaning of the present invention are compounds that are capable of forming hydroxide ions in aqueous solution and of releasing molecular hydrogen during chemical synthesis with base metals. Preferred bases are selected from the group consisting of potassium hydroxide and sodium hydroxide. According to a particularly preferred embodiment of the kit according to the invention, the kit includes magnesium as base metal, preferably in a quantity of 0.1 mg to 20 mg, and as base includes a base selected from the group consisting of potassium hydroxide and sodium hydroxide, preferably in a quantity of 1 mg to 1 g.

The kit according to the invention may include acetylcysteine as another component.

Furthermore, the kit may include adjuvants for an oral form of administration. The abovementioned first and second components of the kit according to the invention may be formulated either together or independently of one another (that is, spatially separated).

Also, the first and second components may be formulated for simultaneous, consecutive, or time-delayed administration within 60 minutes. According to a preferred embodiment of the invention, the kit or its individual components are formulated as a lozenge, tablet, powder, or capsule for direct oral administration or for indirect administration in an aqueous solvent or administration medium.

The gist of the invention will be explained once again in detail below.

The problems addressed by the invention that have been mentioned at the outset are solved by producing hydrogen chemically. At least two components are brought together to start a chemical reaction in which hydrogen is released. In specific embodiments, the acid in the gastric juice or water in the bowel is used as the second component for releasing hydrogen.

Hydrogen can be produced in accordance with the general reaction of acid plus metal reacting to form hydrogen plus salt. Other chemical reactions for producing molecular hydrogen are known. For example, $H^+$ ions (hydron or proton) react with $H^-$ ions (hydride ions) to form $H_2$.

The solution may be that two components are provided in the form of a tablet. Such a tablet may for example consist of the two components metallic magnesium and ascorbic acid. Such a tablet is dissolved in water to produce hydrogen-enriched water.

The problem can further be solved by a powder containing the same composition as the aforementioned tablet.

Furthermore, the production of hydrogen can be coupled with the taking of acetylsalicylic acid, wherein a synergistic effect of the known effects of acetylsalicylic acid and the elimination of ROS in the body can be achieved. In another embodiment, a metal is encapsulated such that it only causes the release of hydrogen after it has been swallowed, in a reaction with the acidic gastric juice in the stomach.

In another embodiment, a hydride is used that is encapsulated and released in a targeted manner in the stomach or bowel. In both cases, the hydride reacts with water or the gastric juice, thereby releasing molecular hydrogen.

Reactive Oxygen Species (ROS)

The reactive oxygen species include the following substances in particular: hyperoxide anion, hydroxyl radical, perhydroxyl radical, peroxy radical, alkoxy radical, hydrogen peroxide, hydroperoxide, ozone, hypochlorite anion, and singlet oxygen.

ROS can be administered to the body externally, as may be the case with ozone. ROS are very often formed and released in the body during inflammatory processes. It is known that the activation of the innate immune system, especially the activation of toll-like receptors (TLRs), results in the release of ROS in the body. These radicals are extraordinarily reactive. It is their biological function to render microorganisms harmless, such as bacteria, fungi, and viruses. But these radicals also react with endogenous substances and cause damage to the body in chronic inflammatory processes. Especially the fact that radicals contribute to the oxidation of phospholipids and to the degradation of hyaluron can have a fatal effect. This results in products that have themselves been proven to activate toll-like receptors, which increases the likelihood of a chronic condition.

In addition to endogenous radicals, humans are exposed to other sources of radicals as well. Certain weather conditions lead to elevated ozone values in the air. Ozone is a significant radical former; numerous people with breathing difficulties and circulatory problems must therefore avoid ozone and should not undertake any physical exertion in the event of elevated ozone levels. Other substances described as leading to the formation of radicals in the body are metals, numerous nanoparticles, and volatile organic compounds (VOCs). VOCs are condensates of an organic nature and often constitute the largest proportion of PM2.5 fine particulates (particles smaller than 2.5 µm). Outside of buildings, industrial combustion processes are the main source of VOCs; in offices these are often laser printers and photocopiers that pollute the air with VOCs, ozone, metals, and nanoparticles.

Another source of radicals is the interaction of ionizing radiation with tissue.

Therapeutically Active Hydrogen

An increasing number of scientific publications documents that the supply of hydrogen by inhalation, drinking of hydrogen-enriched water, or injection of hydrogen-enriched solutions can reduce the amount of free radicals in the body. Patients give subjective reports of effects. They especially report reduced exhaustion. But objective improvement of clinical measurement parameters has also been found after administering hydrogen.

Medical and Non-Medical Indications

There is a large number of relevant clinical indications for administering hydrogen. But hydrogen can also be used for prevention or simply for increasing well-being (wellness) in many cases in which pharmacological intervention is not required.

Infections

The innate immune system is set up particularly to fight bacteria, fungi, and viruses. These are often infectious agents. The response of the innate immune system after contact with these agents or their immunologically relevant components (LPS, DNA, etc.) results in virtually all cases in the release of ROS. It was demonstrated for some infections that mostly have a fatal outcome, such as SARS, the plague, bird flu and the like, that the fatal effect is substantially due to an excessive secretion of ROS (Imai et al., Identification of oxidative stress and Toll-like receptor 4 signaling as a key pathway of acute lung injury, Cell 2008 Apr. 18; 133(2): 235-49). There is a chance here to considerably reduce the mortality of these infections, if the release of ROS can firstly successfully be reduced. ROS already released can be rendered harmless by the administration of hydrogen. This can win valuable time in which the body can develop a specific immune response in the form of antibodies and T-cell receptors. But many people die even from influenza every year, even millions of people in influenza pandemics. Influenza also results in the secretion of ROS. Targeted elimination of ROS through hydrogen can reduce the risk of dying from influenza. Hydrogen can also help mitigate the effects of fungal infections, for example in the case of slow-healing skin eczemas in which fungi and bacteria are often involved.

After Myocardial Infarction and Stroke

Stroke and myocardial infarction always result in the destruction of tissues. However, more tissue is destroyed in the first 5 days after a myocardial infarction or stroke than in the original event. The cause is activity of the innate immune system. Strokes and myocardial infarctions also release large amounts of ROS in localized areas. Hydrogen can therefore help to reduce the further destruction of tissue in the event of stroke and myocardial infarction.

Vascular Sclerosis (Arteriosclerosis), Hypertension

Arteriosclerosis is described as an inflammatory process in the more recent scientific literature. Arteriosclerosis is often accompanied by elevated blood pressure. This inflammatory process also results in the release of ROS. Hydrogen can counteract arteriosclerosis by eliminating ROS.

Multiple Sclerosis (MS)

Multiple sclerosis (MS) is a chronic-inflammatory demyelinating disease of the central nervous system (CNS), the cause of which has not been understood despite great research efforts. It is clear that fatigue is an accompanying symptom of MS in numerous cases. The cause of it is likely usually the release of ROS. The significance of ROS for MS has been described in Ferretti G., Bacchetti T., "Peroxidation of lipoproteins in multiple sclerosis", published in J Neurol Sci. 2011 Dec. 15; 311(1-2): 92-7. Since ROS will also be the underlying cause of fatigue, hydrogen could effect considerable alleviation of symptoms in MS patients.

Depression, Particularly Stress-Induced Depression

Depression has long been considered exclusively a purely neuronal condition. Michael Maes has impressively demonstrated that this is not true. His "leaky gut" theory gives a brief description of this causal chain. Cortisol is released due to prolonged stress. The result is that the bowel becomes leaky to various substances. If the bowel is leaky, bacterial lipopolysaccharides (LPS, also known as endotoxin) can be transferred into the blood. LPS can also cross the blood-brain barrier. In the brain, LPS causes inflammatory processes. The consequence of such inflammation is depression and fatigue. These processes also result in the secretion of ROS. Hydrogen can eliminate these radicals and thus improve the patient's condition. Stress-induced depression is often referred to as "burnout syndrome" in Germany. Hydrogen can especially improve fatigue conditions that are a result of ROS, both subjectively and objectively.

MUS (Medically Unexplained Syndromes)

There is a multitude of medically unexplained syndromes (MUS) which overlap considerably in many symptoms. These include:

| Brain | Throat and mouth |
|---|---|
| Chronic fatigue<br>Depression<br>Concentration disorders<br>Difficulty finding words<br>Unexplained headache<br>Nausea | Throat inflammations<br>Inflammations of vocal chords<br>Burning tongue<br>Reduced sense of taste |
| | Eyes |
| Gastro-intestinal | Burning eyes<br>Skin |
| Stomach pain<br>Diarrhea<br>Ulcerative colitis | Skin rashes<br>"Pins and needles" sensations of the skin, Alopecia |
| Lungs | Extremities |
| Chronic dry cough<br>Asthma<br>Nose | Numbness in hands and feet<br>Muscles |
| Rhinitis<br>Inflammations of the sinuses | Unexplained muscle pain<br>Fibromyalgia<br>Cardiovascular |
| | Hypertension<br>Tachycardia |

It has been demonstrated for may cases that activation of the innate immune system is substantially involved in MUS. Such MUS include but are not limited to: chronic fatigue syndrome, burnout syndrome (stress-induced depression), sick building syndrome (people get sick in offices), fibromyalgia (characterized by muscle pain), multiple chemical sensitivity, irritable bowel syndrome, Crohn's disease, ulcerative colitis, amyotrophic lateral sclerosis (ALS), systemic inflammatory response syndrome, Gulf War illnesses, Ground Zero illnesses, hypersensitivity to laser printers and photocopiers, amalgam disease, vaccine damage, metabolic syndrome, autism spectrum disorders (ASD). Virtually all medically unexplained syndromes are accompanied by massive fatigue. Hydrogen can alleviate the symptoms for fatigue conditions that are mainly due to ROS.

Ionizing Radiation

Ionizing radiation can generate radicals in tissue. Radicals can result in products such as oxidized phospholipids and metabolites of hyaluron, which activate the TLR4 receptor. Activation of the TLR4 receptor leads to ROS at the end of a causal chain.

X-Ray

X-radiation is often used in the radiation therapy of tumors (cancer). Roughly 50% to 90% of treated patients suffer from massive fatigue for months, even for years, as a result of the therapy. Large amounts of radicals are generated in the tissue during irradiation. Treatment with hydrogen can reduce the subsequent fatigue conditions. The administered hydrogen does not adversely affect the actual therapy.

Radioactivity

Radioactivity also produces free radicals in tissue. The symptoms after irradiation with radioactivity are the same as after X-ray therapy and the symptoms as reported for MUS. Administering hydrogen during and after exposure to radioactivity can help reduce indirect radiation damage.

UV

Exposure to UV light (sunbathing, tanning studio, therapeutic irradiation with UV light) generates radicals. This damage by UV light can be reduced using hydrogen. It is useful to take the hydrogen before the exposure. Hydrogen should also be applied during and after exposure to UV light.

Alcohol Consumption and Alcohol Abuse

The literature states that alcohol consumption leads to activation of the innate immune system. Direct and indirect mechanisms are at work here. Continued alcohol consumption also makes the bowel permeable to LPS. Activation of the innate immune system results in the release of ROS. ROS is presumably substantially involved in the headaches after excessive alcohol consumption. Administering hydrogen can alleviate the harmful processes attributable to ROS by rendering the ROS harmless.

Sports and Physical Exercise (Sore Muscles)

It was a surprising finding that excessive physical exercise leads to activation of the innate immune system. This results in sore muscles. Development of sore muscles can largely be avoided by taking hydrogen.

High Ozone Pollution of the Environment

Individuals who are particularly sensitive to ozone pollution can improve their personal radical balance considerably through intake of hydrogen. Hydrogen can help people having circulation problems and older people to better withstand situations in which ozone values are high. In interior spaces, some devices, particularly photocopiers and laser printers, generate significant ozone concentrations that can clearly be perceived. About 19 million people in Germany work in offices. Many of them are exposed to elevated ozone concentrations from these office machines.

Hydrogen

Hydrogen is unproblematic for the body in the envisaged quantities. It is completely non-toxic and rather chemically inert when dissolved in tissue fluids. Only chemical radicals, particularly ROS, react with hydrogen in the body. The products formed in this way are less toxic than ROS and are broken down by the body.

At least two reactants are always required to produce hydrogen chemically. At least one reactant must always be supplied. The second reactant can be a substance provided separately, or endogenous substances are used as reactants. There are numerous chemical reactions to generate hydrogen. Two important reactions take place according to the following general chemical equations $$Acid + metal \rightarrow H_2(g) + salt \quad (1)$$

$$H^+ + H^- \rightarrow H_2(g) \quad (2)$$

Under standard conditions (room temperature, standard air pressure) hydrogen dissolves in water at a maximum concentration of about 0.8 mmol. Since one mole of hydrogen ($H_2$) has a mass of 2 g, this corresponds to about 1.6 mg of hydrogen per liter of water. Despite this relatively low mass, 0.8 millimole of hydrogen still amounts to about $4.8*10^{20}$ hydrogen molecules. It would be sufficient to achieve a therapeutic effect in the cases described if the hydrogen saturation of the water was under 50% and amounts of one liter were consumed. The lower limit of hydrogen that has to be supplied to the body to still achieve detectable positive effects has not yet been exactly quantitatively determined. But it can safely be assumed that a quantity of 0.4 mmol or 0.8 mg of hydrogen per day is pharmacologically effective. The advantage of the small masses required is that substances can be used for generating hydrogen that do not deliver quantities of more than 100 mg per day to the body. This makes it possible, for example, to use magnesium or calcium, wherein individuals can consume these metals without expecting any adverse side effects.

The following table lists the European Recommended Daily Allowance values (EU-RDA) for vitamin C and some metals:

| | |
|---|---|
| Vitamin C 80 mg | Copper 1 mg |
| Calcium 800 mg | Magnesium 375 mg |
| Iron 14 mg | Manganese 2 mg |
| Potassium 2000 mg | Zinc 10 mg |

The invention will be described briefly below with reference to exemplary embodiments.

EXEMPLARY EMBODIMENTS

Example 1

Magnesium+Ascorbic Acid (Vitamin C)

Reaction Equations:

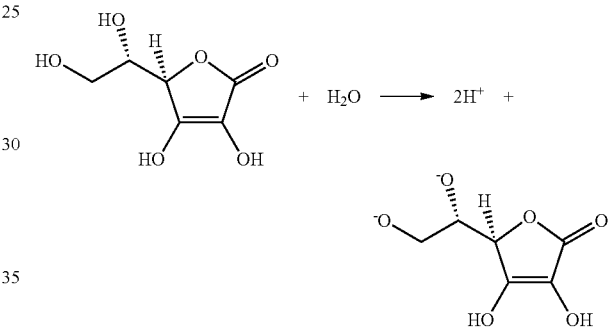

$$Mg + 2H^+ \rightarrow Mg^{2+} + H_2(g)$$

As a Powder 19.4 mg magnesium and 240 mg ascorbic acid (as vitamin C in the L-(+)-ascorbic acid conformation) are added to one liter of water. The magnesium is preferably provided in the form of magnesium powder with a grain size of 0.3 mm and smaller. It is preferred that the ascorbic acid is a powder as well. Both substances sink to the bottom. Since ascorbic acid dissolves slowly in water, a local high concentration of ascorbic acid develops at the bottom of the vessel. Formation of gas bubbles commences visibly. The gas bubbles consist of molecular hydrogen. This hydrogen partially dissolves in water, which is visible directly in that the bubble size decreases. The reaction takes about 5 minutes to minutes, depending on the size of the magnesium particles. The water enriched with hydrogen in this manner is drunk to administer the hydrogen.

The quantities of both magnesium and ascorbic acid can be varied. It appears to be useful for enriching one liter of water with hydrogen to use magnesium quantities from 0.1 mg to 20 mg and ascorbic acid quantities from 1 mg to 1 g. Other quantities may still prove to be pharmacologically effective. Preferred are 20 mg magnesium together with 240 mg ascorbic acid for producing one liter of hydrogen-enriched water.

The mixture of magnesium powder and ascorbic acid powder can be packaged airtight in bags for the market. If it should be found that a reaction of the two substances takes place during prolonged storage, for example due to residual humidity, the two substances may be packed in separate compartments of the bag. Separation may also be achieved by coating the magnesium with an adjuvant, such as a sugar, a starch, a gelatin, and other suitable methods known from prior art for separating two pharmacological substances.

Ascorbic acid is known as vitamin C and is preferably used to capture free radicals in the body.

The combination of vitamin C with the generated hydrogen has a synergistic effect in this sense, since both eliminate radicals in different ways. Magnesium is capable of displacing heavy metals in the body. The combination of magnesium and ascorbic acid therefore leads to three benefits: two substances that render radicals harmless and the displacement of heavy metals.

As a Tablet

A mixture of ascorbic acid and magnesium can also compressed into tablets. The tablets can be packaged in common blisters or tubes. Again, if prolonged storage is required, magnesium and ascorbic acid can also be separated by an adjuvant in the form of a tablet using the typical means of prior art. A tablet, as a compact and very common form of application, is the preferred embodiment for the preventive taking of hydrogen.

The adjuvants and processes known from prior art may of course be utilized for manufacturing a magnesium-ascorbic acid tablet.

The adjuvants that may be required for tableting, particularly for direct tableting, in particular fillers, binding agents, disintegrants and lubricants are known to a person skilled in the art (see, for example, the book by Annette Bauer-Brandl and Wolfgang A. Ritsche, "Die Tablette, Handbuch der Entwicklung, Herstellung and Qualitätssicherung" 2012, 3rd revised and extended edition, ISBN-10: 3871934070).

Example 2a

Magnesium+Acetylsalicylic Acid

Acetylsalicylic acid, known worldwide under the brand name Aspirin from Bayer AG, is also an acid. Acetylsalicylic acid is also excellently suited for producing hydrogen in combination with magnesium.

For example, a preparation of 4 mg of magnesium (powdered) and 400 mg of acetylsalicylic acid can be prepared. It is dissolved in 200 mL of water. The reaction time for forming hydrogen depends primarily on the size of the magnesium particles. It is preferred to use small magnesium particles, e.g. a grain size of 0.1 mm or smaller. The smaller the particles, the faster hydrogen is formed.

The preparation is drunk to supply the pharmacological substances acetylsalicylic acid and hydrogen to the body. This combination is particularly well suited to fight headaches that occur, for example, after consuming alcohol. But numerous other pains, such as the pain that occurs with fibromyalgia, or other impairments, such as the symptoms that accompany influenza, can be treated with the combination of hydrogen and acetylsalicylic acid. This embodiment is the preferred embodiment for treating more serious symptoms, when a combination with acetylsalicylic acid is indicated.

Dissolution in water is not strictly necessary. When swallowed, the tablet dissolves in the stomach and generates the hydrogen there. If this happens slowly, the hydrogen should remain in the body. No violent belching is expected, since 4 mg of magnesium only generate about 4 mL of hydrogen gas.

Magnesium can of course be combined with several acids at the same time. Acetylsalicylic acid is frequently supplied in combination with ascorbic acid (e.g. as Aspirin plus C®). According to the manufacturer, this preparation contains 400 mg of the active ingredient, acetylsalicylic acid, and 240 mg of vitamin C. In addition, 1 mg to 10 mg magnesium per dose could be added to the formulation, for example. This would yield a particularly effective, anti-inflammatory, analgesic and radical-absorbing medicinal product.

Example 2b

Magnesium+Acetylsalicylic Acid+Vitamin C (Aspirin Plus C® in Combination with Magnesium)

400 mL of cold drinking water are provided. 20 mg of metallic magnesium in powder form are added. The grain size should be 0.3 mm or smaller so that the reaction can take place quickly because more reactive surface is available. But this size is not obligatory. Then one Aspirin plus C® tablet is added. This effervescent tablet dissolves. The solution is so acidic that the magnesium reacts, forming fine hydrogen bubbles. After about 10 minutes, the reaction was substantially complete, and the solution is enriched with hydrogen and ready for taking. This should be a much improved formulation. The combination of active ingredients here has a synergistic effect:

Aspirin: anti-inflammatory, blood-thinning, and analgesic

Vitamin C: acts as radical scavenger

Hydrogen, currently probably the best radical scavenger for ROS

Magnesium displaces heavy metals in the body, is an essential mineral

The order in which water, magnesium, and Aspirin plus C® are mixed is not important.

Example 3

Magnesium+5-Aminosalicylic Acid (5-ASA)

5-Aminosalicylic acid (5-ASA), also known under the brand name Mesalazin®, is a standard drug for treating ulcerative colitis, Crohn's disease, and irritable bowel syndrome. Chronic inflammatory processes play a major role in these conditions. These conditions also result in the formation and release of ROS. Therapy with hydrogen can therefore help to alleviate the symptoms. There are numerous ways of supplying hydrogen to the body. In the case of these intestinal diseases, it can be advantageous to undertake hydrogen release in a targeted manner in the bowel. For example, capsules resistant to gastric juice as known from prior art can be used here. 5-aminosalicylic acid can be used as the acid that releases hydrogen when reacting with magnesium. But the solubility of 5-ASA in water is very low, such that the acidic effect is not sufficient, particularly in the alkaline environment of the bowel. Therefore, another acid, such as acetylsalicylic acid or ascorbic acid, should preferably be added to the capsule. Other acids are in principle suitable as well. A therapeutic synergistic effect can be achieved by combining 5-aminosalicylic acid with hydrogen.

Example 4

Magnesium+Tartaric Acid/Citric Acid/Acetic Acid

The generation of hydrogen is not limited to the acids mentioned before. In principle, any acid that is strong enough to start the reaction with magnesium with release of hydrogen is suitable. However, many strong acids, such as sulfuric acid or phosphoric acid, are less suitable because they are difficult to handle and cause caustic burns in excessive quantities. Acids with volatile gases such as hydrochloric acid, formic acid, or acetic acid can also produce hydrogen together with magnesium. But these acids are not particularly easy to use industrially for making tablets and the like either. Therefore, preferably solid acids that are additionally approved for human consumption are preferred. These include, for example, citric acid and tartaric acid.

Metals

The production of hydrogen is not just limited to magnesium; hydrogen can generally be produced from the combination of an acid and a metal. There are strict limitations in all cases in which the reaction mixture is supplied to the body. All toxic heavy metals such as lead, mercury, cadmium, arsenic and the like are excluded because of their toxicity. Metals that are beneficial on the milligram scale include sodium, potassium, calcium, manganese, zinc, and iron. Sodium and potassium are of limited suitability due to their violent reaction with water. The chemical reaction should be delayed by a slow-release formulation when these are used. This applies similarly to calcium. Manganese may only be supplied at very small doses because greater quantities cause numerous side effects. Zinc and iron are still suitable, but they require strong acids to bring about the release of hydrogen.

Other metals may be used in similar ways as in the exemplary embodiments mentioned above to provide preparations for producing therapeutically active hydrogen. Apart from the ones mentioned above, beryllium, titanium, manganese, tin, boron, aluminum can be considered in small quantities, but for various reasons these are not preferred embodiments.

Pure Metallic Magnesium

In principle, use of an acid can be dispensed with if the preparation is designed such that a reaction with the hydrochloric acid contained in the gastric juice takes place. For example, 20 mg of magnesium can be formulated such that it can be swallowed with ease. A gelatin capsule that dissolves in the stomach is suitable for this, for example. The magnesium reacts with the gastric juice with release of hydrogen. Other suitable metals can be used instead of magnesium, such as sodium, potassium, calcium, manganese, zinc, and iron.

Metals Suitable in Principle

In principle, useful metals are all those that release hydrogen in a reaction with an acid. Apart from the ones mentioned before, these are, for example: lithium, sodium, potassium, beryllium, titanium, manganese, iron, tin, boron, aluminum. Mixtures and alloys of metals may also be considered, of course.

Hydrides

Hydrogen can also be produced according to the general reaction formula:

$$H^+ + H^- \rightarrow H_2(g).$$

Many hydrides are extremely reactive, such that contact with water is sufficient to release hydrogen. For example, NaH reacts with water to give $H_2$ (g) and NaOH.

Magnesium Hydride

Magnesium hydride is particularly suitable for production of therapeutically active hydrogen in combination with water or an aqueous acid. For example, 40 mg of pure magnesium hydride can be encapsulated such that the capsule will not dissolve until the stomach. A gelatin capsule would be suitable for this, for example. The following reaction takes place in the stomach:

$$MgH_2 + 2H^+ \rightarrow H_2 + Mg^{2+}$$

Similarly, magnesium hydride can be packaged in a capsule resistant to gastric juice, which will not decompose until the bowel. When it comes into contact with water in the bowel, the desired release of hydrogen takes place. Analogously, hydrogen can be produced in a targeted manner in the stomach or bowel using sodium hydride and potassium hydride.

Hydrides can of course be used to produce hydrogen-enriched water for drinking. The bases that are formed in the process, such as NaOH and KOH, can be neutralized by adding equimolar quantities of acid, such as ascorbic acid, tartaric acid, or acetic acid.

Hydrides Suitable in Principle

In principle, all hydrides, particularly metal hydrides, can be used to release hydrogen. Metals are subject to the same limitations that were mentioned in the embodiments above.

Example 5

Acetylcysteine
(L-α-Acetamido-β-Mercaptopropionic Acid)+Hydrogen, e.g. from Magnesium+Acid

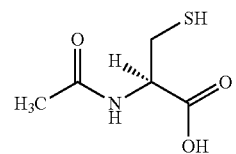

Structural Formula of Acetylcysteine (Trade Names ACC and NAC)

The relevant scientific literature states that acetylcysteine is capable of neutralizing free radicals in tissue. In addition to hydrogen, acetylcysteine therefore is a second active agent that can eliminate radicals. Since the molecular mechanisms for the two substances are different, a synergistic effect can be achieved if hydrogen is administered together with acetylcysteine.

Since acetylcysteine reacts with water to give a slightly basic solution, an acid must be added if hydrogen is to be produced using magnesium. For example, 20 mg of magnesium in powder form are mixed with 240 mg of ascorbic acid in 500 mL of water. After 10 minutes, 200 mg of acetylcysteine are added and dissolved.

Another acid may be used as a replacement for ascorbic acid, e.g. tartaric acid or citric acid.

Hydrogen and acetylcysteine may of course also be administered consecutively. It is not required that both substances must be present in the same solution. The time in between should not be more than one hour.

It can be useful for a continuous titer to administer acetylcysteine and hydrogen at least three times a day. Hydrogen-enriched water may also be administered without any problem throughout the day in quantities of up to 2 liters.

If patients are fed via a gastric tube, both substances can also be supplied via this tube. Combined administration of hydrogen and acetylcysteine can contribute to bringing the excessive production of ROS under pharmacological control, particularly in very severe infections (influenza, bird flu, plague, etc.). But massive fatigue conditions, as occur in burnout syndrome, for example, can in many cases also be overcome quickly (within days) by giving hydrogen or by giving a combination of hydrogen and acetylcysteine.

Example 6

Multivitamin Preparations Supplemented with Magnesium

Effervescent tablets that supply a multitude of vitamins and minerals as nutritional supplements are very common. A typical multivitamin preparation in the form of an effervescent tablet can additionally be supplemented with 20 mg of powdered magnesium. It is important that the pH set by the effervescent tablet is in the acidic range for hydrogen to be produced from the reaction of the acid with the metal.

Example 7

Hydrogen from Magnesium+Base

Bases such as sodium hydroxide can also be used to produce hydrogen from magnesium in aqueous solution.

The reaction may take place, for example, according to the equation $$2Mg+4NaOH \rightarrow 2MgO+Na_2O+H_2(g)$$

$$Na_2O+H_2O \rightarrow 2NaOH$$

Other bases can be used as well. The sodium hydroxide must be neutralized with an acid for producing hydrogen-enriched water for human consumption in this way. This can be achieved, for example, using an equivalent quantity of hydrochloric acid, ascorbic acid, tartaric acid, etc. Of course, other bases such as potassium hydroxide may be utilized as well.

The invention claimed is:

1. A kit for prophylaxis or treatment of oxidative stress in humans and animals, wherein the kit comprises a first component including a base metal for targeted chemical synthesis of therapeutically active hydrogen molecules by reaction with aqueous acid, and a second component, wherein the second component includes at least one acid which is chemically inert with respect to the base metal of the first component, wherein the kit includes adjuvants for an oral form of administration, and wherein the kit includes 0.1 mg to 20 mg magnesium as said base metal, and 1 mg to 1 g of acetylsalicylic acid as said acid in the second component.

2. The kit according to claim 1, characterized in that therapeutically active hydrogen molecules are formed by combining the base metal with the acid under aqueous conditions.

3. A kit for prophylaxis or treatment of oxidative stress in humans and animals using therapeutically active hydrogen molecules, wherein the kit comprising a first component including a base metal for targeted chemical synthesis active hydrogen molecules by reaction with an aqueous base, and a second component includes at least one base which is chemically inert with respect to the base metal of the first component, wherein the kit includes 0.1 mg to 20 mg magnesium as said base metal, and 1 mg to 1 g of said base selected from the group consisting of potassium hydroxide and sodium hydroxide.

4. The kit according to claim 3, characterized in that the therapeutically active hydrogen molecules are formed by combining the base metal of the first component with an aqueous base of the second component.

5. The kit according to claim 3, characterized in that the kit includes acetylcysteine as another component.

6. The kit according to claim 1, characterized in that the first component is formulated jointly with, or independently from, the second component.

7. The kit according to claim 6, wherein the first and second components are formulated for simultaneous, consecutive, or time-delayed administration within 60 minutes.

8. The kit according to claim 3, characterized in that the first component is formulated jointly with, or independently from, the second component.

9. The kit according to claim 8, wherein the first and second components are formulated for simultaneous, consecutive, or time-delayed administration within 60 minutes.

10. The kit according to claim 1, wherein the kit or its individual components are formulated as a lozenge, tablet, powder, or capsule for direct oral administration or for indirect administration in an aqueous solvent or administration medium.

11. The kit according to claim 3, wherein the kit or its individual components are formulated as a lozenge, tablet, powder, or capsule for direct oral administration or for indirect administration in an aqueous solvent or administration medium.

12. The kit of claim 2, wherein when the base metal or saline hydride is combined with with the acid under aqueous conditions and administered to a human or animal, at least 0.4 mmol or 0.8 mg of molecular hydrogen per day is supplied to the human or animal.

13. The kit of claim 4, wherein when the base metal of the first component is combined with the aqueous base of the second component and administered to a human or animal, at least 0.4 mmol or 0.8 mg of molecular hydrogen per day is supplied to the human or animal.

* * * * *